United States Patent [19]

Mancilla et al.

[11] Patent Number: 5,399,318

[45] Date of Patent: Mar. 21, 1995

[54] BLOOD SAMPLING APPARATUS CONTAINING AN ANTICOAGULANT COMPOSITION

[75] Inventors: Edward Mancilla, Waunakee, Wis.; Elizabeth M. Lagwinska, Chesterfield, Mo.

[73] Assignee: American Home Products Corporation, Madison, N.J.

[21] Appl. No.: 236,283

[22] Filed: May 2, 1994

Related U.S. Application Data

[60] Division of Ser. No. 96,123, Jul. 22, 1993, Pat. No. 5,336,620, which is a continuation of Ser. No. 9,627, Jan. 27, 1993, abandoned.

[51] Int. Cl.6 .................... B01L 3/02; A61K 31/725
[52] U.S. Cl. .................................... 422/100; 422/102; 436/18; 604/266; 128/763
[58] Field of Search ................ 422/44, 100, 102; 436/18; 514/56; 604/52, 126, 190, 266; 128/760, 763–765

[56] References Cited

U.S. PATENT DOCUMENTS

| | | | |
|---|---|---|---|
| 3,337,409 | 8/1967 | Williams et al. | 536/21 |
| 4,595,021 | 6/1986 | Shimizu et al. | 128/760 |
| 4,680,177 | 7/1987 | Gray et al. | 424/101 |
| 5,039,529 | 8/1991 | Bergendal et al. | 424/630 |
| 5,104,860 | 4/1992 | Piani et al. | 514/56 |

Primary Examiner—Jeffrey R. Snay
Attorney, Agent, or Firm—Steven H. Flynn

[57] ABSTRACT

Disclosed is a blood sampling apparatus containing an anticoagulant composition which allows for the accurate analysis of blood electrolyte concentrations. The claimed apparatus comprises a receptacle, a blood inlet and the disclosed anticoagulant composition which does not unduly bind sodium, potassium or calcium ions from the sampled blood.

19 Claims, 1 Drawing Sheet ly from the same invention being an appellant composition.

BLOOD SAMPLING APPARATUS CONTAINING AN ANTICOAGULANT COMPOSITION

This is a divisional of U.S. Ser. No. 08/096,123, filed on Jul. 22, 1993, now U.S. Pat. No. 5,336,620, which is a continuation of U.S. Ser. No. 08/009,627, filed on Jan. 27, 1993, now abandoned.

FIELD OF THE INVENTION

The present invention relates to a process for the production of an anticoagulant composition, as well as the composition so produced. The present invention further relates to an apparatus containing such composition for use in the sampling of blood and a method of sampling blood.

BACKGROUND OF THE INVENTION

The analysis of whole blood requires the use of an anticoagulant, typically in the collection apparatus, in order to prevent coagulation of the collected blood sample prior to its analysis. The use of heparin, both in dry and liquid form, is known, as is its ability to bind a certain portion of the electrolyte within the blood sample (e.g. sodium, potassium and/or calcium ions). This electrolyte binding is undesirable since it effectively prohibits an accurate analysis of blood electrolyte concentration, particularly sodium, potassium and calcium ion concentrations. The measurement of calcium ion concentration has recently received increased attention in the field of cardiac medicine in view of the heart's sensitivity to calcium ion concentration and the recent development of blood gas machines to monitor the concentration thereof.

Various solutions to the problems associated with this electrolyte binding by heparin have been heretofore proposed. For instance, Radiometer SA of Copenhagen has previously marketed anticoagulant compositions for use in connection with blood sampling apparatus in the form of capillary tubes having a coating on the inner wall of the tube of dry sodium heparinate. These compositions are further said to contain a specified amount of calcium chloride in an effort to compensate for the blood's calcium anions which will be bound by the heparinate once in solution. The use of this composition therefore does not provide a complete solution to the aforementioned problem since this composition introduces additional sodium and chloride ions into the blood sample, thereby altering an accurate analysis of the concentration of sodium and chloride within the blood sample. Moreover, the added calcium ions represent only a replacement for an approximation of those expected to be bound by the heparin component. Therefore, an analysis for calcium ion concentration within the collected sample while improved, is not rendered totally accurate.

U.S. Pat. No. 4,687,000 (assigned to Radiometer A/S) discloses a method for treating a blood sample with an anticoagulant as well as a blood sampling device. The disclosed method involves contacting a collected blood sample with (a) an anticoagulant capable of binding cation species within the blood and (b) an additive including selected cationic species in the amounts compensating for proportions of these cation species bound by the anticoagulant. The disclosed method still does not represent a true solution to the aforementioned problems, however, since again the cationic species present in the additive represent only estimations of the cations expected to be bound rather than the true and exact amounts.

It is therefore an object of the present invention to provide a process for the production of an anticoagulant composition.

It is further an object of the present invention to provide a method for treating blood with anticoagulant which allows for accurate analysis of the sodium, potassium and calcium ions present therein.

It is further an object of the present invention to provide an apparatus which is both a container for the claimed anticoagulant and useful in the practice of the claimed method.

SUMMARY OF THE INVENTION

The present invention comprises a process for the production of an anticoagulant and the anticoagulant produced thereby.

The present invention further is directed to a blood sampling device comprising
 (a) a receptacle means defining a blood receiving space therein for receiving a blood sample;
 (b) a blood inlet means for introducing a blood sample into the blood receiving space; and
 (c) an anticoagulant present within said blood receiving space, said anticoagulant comprising the product of the process of claim 1.

The present invention further comprises a method for collecting blood samples through use of the claimed composition.

DETAILED DESCRIPTION OF THE PRESENT INVENTION

Figure 1:
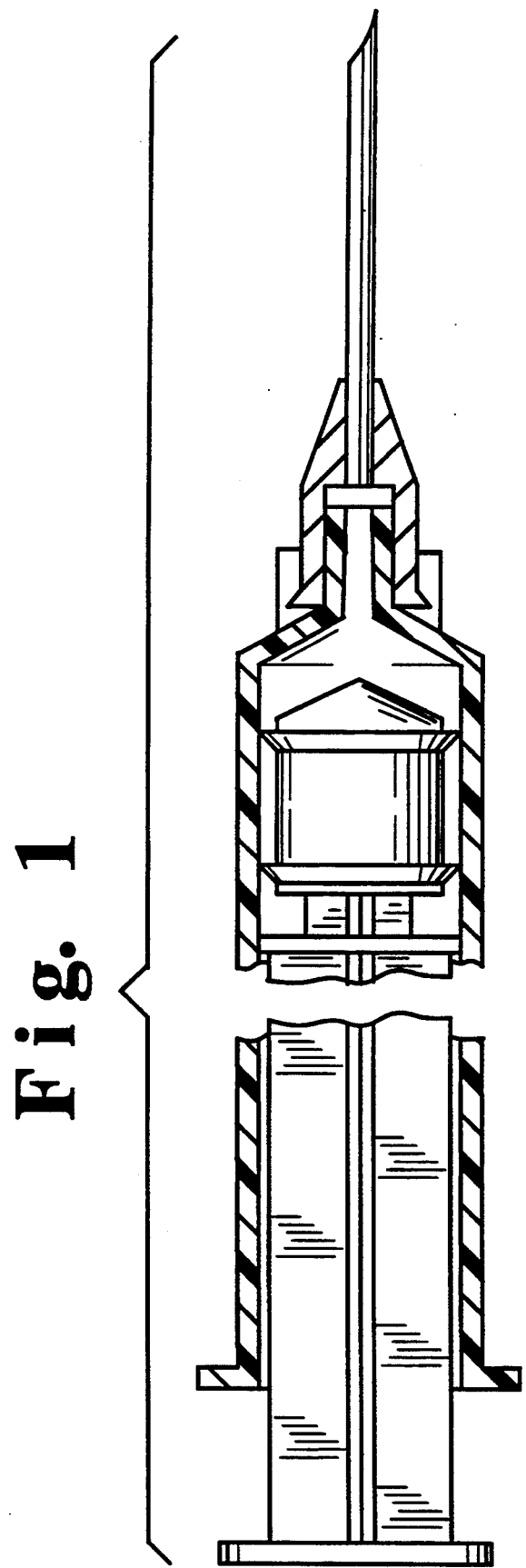
FIG. 1 is a cross-section of a syringe useful in the practice of the present invention as a blood collection device. The syringe provides a receptacle means defining a blood receiving space and a blood inlet means for introducing a blood sample into the blood receiving space.

As stated above, the present invention relates to a novel anticoagulant composition and the process for its production. The invention further relates to an improved method for the collection of blood samples and an apparatus useful in the practice thereof.

The anticoagulant composition of the present invention is lithium heparinate modified with a heavy metal salt such as zinc acetate. It is produced through a procedure which is outlined below.

A quantity of sodium heparin is obtained and dissolved in water to a consistency such that it is suitable for passage through a bed of an ion exchange resin. Sodium heparin is obtained from various sources such as beef lungs and/or mucosa, pork mucosa, and whole pork intestines. It is further commercially available from such sources as Viobin Corporation of Waunakee, Wisconsin. Preferably, the solution so formed has a concentration of about 30,000 to about 50,000 u/cc.

The solution is then passed through a column of an acidic ion exchange resin. The resin may comprise any acidic ion exchange resin or mixtures thereof. Such resins include IR-120 (a resin available from Rohm and Haas Company having a matrix structure of divinylbenzene (8%) and a sulfonic acid functionality). Preferred is the IR-120 resin. Especially preferred is the use of IR-120 resin in the hydrogen form. The effluent from the ion exchange column is collected and monitored for the presence of heparin such as through the use of toluidine blue. The effluent should further possess a pH of 3 or less. The acidity of the effluent can be maintained through adjustment of the residence time of the solution within the ion exchange column.

The acidic heparin effluent is then converted to a heavy metal heparin salt through contact with a heavy metal-containing compound. Conversion to a zinc, barium or copper salt is preferred. These salts include zinc acetate dihydrate as well as the chlorides and sulfates of zinc, barium and copper. Use of zinc acetate dihydrate is preferred. In the case where zinc acetate dihydrate is used, it is added to the acidic effluent in an amount ranging from about 2 to about 7 grams, preferably about 5 grams, per each 15 grams of sodium heparin originally introduced into the ion exchange column. Use of other of the above-named heavy metal containing compounds include the use of similar molar amounts. The pH solubility of the solution is further monitored to ensure that the pH is maintained so as not to exceed about 3.

To the heparin-heavy metal salt produced in the preceding step is then added an aqueous solution of lithium salts such as lithium acetate, lithium hydroxide or lithium carbonate such that the resulting solution possesses a pH in the range of about 6 to about 7. The use of lithium hydroxide is preferred. Use of an aqueous 10% lithium hydroxide solution is especially preferred. This solution is agitated, typically for a period of about 4 to about 24 hours, preferably at least 8 hours, to permit for chelation of the lithium and stabilization of the solution's pH. Additional amounts of either solution may of course be added to correct for pH deviations.

The pH stabilized solution may then be filtered through a filter media suitable to remove any bacterial contamination and/or insoluble matter picked up during prior processing. Use of a media having a pore size of about 0.22 microns is preferred. The filtered solution may then be dried in a suitable apparatus such as a Lyophilizer produced by Hull or Virtis.

Drying times and temperatures should be maintained at a level such that undue degradation of the heparinate composition is avoided. Once dried, the heparin composition should further be preferably stored in an area of low humidity in view of the hydroscopic nature of the material.

The claimed composition is found to possess about 6 to about 8% by weight of zinc through atomic absorption spectroscopy. If heavy metals other than zinc were used, the claimed composition contains equivalent molar amounts of such metals.

The amount of the heparin composition used in conjunction with sampled blood should be sufficient to ensure against coagulation of the blood sample. However, use of great excesses of the composition should also be avoided in order to minimize any potential interference in the analysis of the collected blood sample. It is therefore preferred that use be made of the least amount of the anticoagulant composition which adequately prevents blood sample coagulation. It has been found, for example, that the use of about 8 to about 150 international units (IU) of the composition per milliliter of sampled blood is useful in the practice of the claimed method. Preferably, about 20 to about 80 IU/ml are used. Most preferably, about 50 IU/ml are used. The above quoted ranges for the concentration of anticoagulant adequate to prevent blood coagulation are concentrations which are recognized as useful in collection devices and indeed are present in products which are currently commercially available. These ranges do not however refer to use in Sherwood ABG syringes described herein.

However, it should be noted that lower concentrations of anticoagulant are being increasing used and recommended. For instance, the proposed guidelines issued in September 1992 by the NCCLS subcommittee on Electrolytes (Document C31-P) recommends the use of heparinate in an amount of about 15 IU/ml. Lower concentrations (e.g. below 10 IU/ml) have also been reported as sufficient. Indeed Sherwood Medical ABG syringes currently contains 12 (+/−2) IU/ml of heparinate. Use of such lower levels of anticoagulant is within the scope of the present invention.

The claimed anticoagulant composition may be pre-dissolved prior to its being contacted with a collected blood sample or, more preferably, utilized in its dried state wherein it is dissolved upon its contact with the collected blood sample. Most preferably, the composition is present in dried form within the collection apparatus for the blood sample, i.e. capillary tube, syringe or vacuum container. In this way, it is available for immediate contact with the sampled blood as it is collected. The dried form of the claimed composition may be present within the collection apparatus as a free solid (i.e. powder) or as a film or coating present on the walls or other internal structure of the collection apparatus. For instance, the composition may be deposited on or within an inert carrier body, such as disclosed in U.S. Pat. No. 4,687,000, the contents of which are hereby incorporated by reference.

The invention disclosed herein is further described through the following illustrative examples. Such examples are not intended, nor should they be construed, as limitations to the scope of the present invention.

EXAMPLE I

Approximately one kilo of sodium heparin (manufactured by the Viobin Corporation) is dissolved to form an aqueous solution having a concentration of 30,000 to 50,000 u/cc.

A column of about 9 liters of IR-120 Plus ion exchange resin in the hydrogen form is prepared and then washed with a sufficient quantity of water. The heparin solution is then introduced into the column and the pH of the effluent is monitored with Toluidine Blue. The pH of the effluent is maintained at 3 or less. The effluent is collected.

Zinc acetate dihydrate is added to the collected effluent in an amount of about 3 to about 7 grams of the zinc salt per each 15 grams of the starting amount of sodium heparin. A sufficient amount of a 10% aqueous solution of lithium hydroxide is added such that the resulting solution has a pH of about 6.0 to about 6.5. The solution is then allowed to settle overnight. In the morning, the solution is filtered through a 0.22 micron filter media. The solution is dried through the use of a Hull Lypohizer and the resulting product is stored in a low humidity area.

EXAMPLE 2

A stock solution of the heparin composition produced in Example 1 is prepared by dissolving about 1,440,000 USP units in about 1,000 ml of deionized water. The resulting solution possesses about 1,440 USP units/mi.

By means of a pipette, 0.025 ml of the heparin solution is placed in a syringe (ABG brand manufactured by Sherwood Medical) in the 45° crease in the barrel. The solution is then dried by means of the lyophilization method. The dried heparinate cakes in the syringe contain about 36±6 USP units of heparinate. The final heparin concentration in blood samples collected in these syringes should therefore be in the range of 12±2 USP units/ml.

The syringes are then used in the collection of blood. The syringes are filled completely and/or partially with blood and the specimens are then analyzed for electrolytes. Similar quantities of blood are also collected in heparin-containing syringes manufactured by Radiometer (type Smooth-E Arterial Blood Sampler) and Sherwood Medical (Type ABG) as well as a syringe having no heparinate contained therein (control).

The test results and a summary of a statistical analysis of said results are presented in Tables 1, 2 and 3.

ing to ionized calcium at all blood volumes and acceptable slopes an intercepts. Heparin interference with quantifiying ionized calcium concentration even when the proportion of heparin was effectively increased by partially filling the syringe with sampled blood was therefore reduced. Similar results were exhibited with Syringe C. As expected, syringes containing plain lithium heparin (Syringe B) exhibited significantly lower ionized calcium values relative to the control data, presumably due to binding of calcium ions with the heparin.

EXAMPLE 3

The procedure of Example 2 was repeated except that the samples were then tested for potassium concentration rather than ionized calcium concentration. The results of Example 3 are presented in Table 2.

TABLE I

Comparison of Ionized Calcium Values Obtained from Blood Specimens Collected in Plain Syringes (Control) Versus Heparinized Syringe Types with Varied Draw Volumes.

| Syringe | Draw Volume ml | X (±SD)$^a$ mg/dL | Comparison to Plain Syringe | | | |
|---|---|---|---|---|---|---|
| | | | Slope | Intercept | Correl Coef | p = |
| Control | | 4.87 (±0.12) | | | | |
| A | 3.0 | 4.91 (±0.11) | 1.02 | −0.12 | 0.95 | 0.02 |
| | 1.0 | 4.93 (±0.11) | 1.02 | −0.17 | 0.96 | <0.01 |
| | 0.75 | 4.91 (±0.10) | 1.19 | −0.99 | 0.94 | 0.02 |
| B | 3.0 | 4.79 (±0.11) | 1.06 | −0.21 | 0.94 | <0.01 |
| | 1.0 | 4.59 (±0.12) | 0.98 | 0.39 | 0.93 | <0.01 |
| | 0.75 | 4.48 (±0.14) | 0.83 | 1.14 | 0.93 | <0.01 |
| C | 3.0 | 4.83 (±0.11) | 0.87 | 0.68 | 0.82 | 0.08 |
| | 1.0 | 4.85 (±0.11) | 1.02 | −0.09 | 0.92 | 0.21 |
| | 0.75 | 4.86 (±0.10) | 1.05 | −0.22 | 0.89 | 0.66 |

$^a$n is 10 for all syringe types

TABLE 2

COMPARISION OF PLASMA POTASSIUM VALUES OBTAINED WITH VARIED DRAW VOLUMES

| SYRINGES | DRAW VOLUME (ml) | N = | X (±SD) (mmol/L) | Comparison to Control Syringes | | | |
|---|---|---|---|---|---|---|---|
| | | | | SLOPE | INTERCEPT | CORREL COEF. | P = |
| Control | | 9 | 4.2 ± 0.2 | | | | |
| A | 3.0 | 9 | 4.1 ± 0.2 | 0.64 | 1.5 | 0.75 | 0.50 |
| | 0.75 | 8 | 4.1 ± 0 | 0.74 | 1.1 | 0.79 | 0.33 |
| B | 3.0 | 9 | 4.1 ± 0.2 | 0.76 | 1.0 | 0.77 | 0.5 |
| | 0.75 | 9 | 4.2 ± 0.2 | 0.52 | 2.0 | 0.50 | 0.88 |
| C | 3.0 | 0 | 4.2 ± 0.1 | 0.55 | 1.9 | 0.78 | 0.35 |
| | 0.75 | 9 | 4.4 ± 0.3 | 0.77 | 1.1 | 0.64 | 0.02 |

A represents a 6 ml (3 ml draw) syringe manufactured by Sherwood Medical Company which contains the lithium heparinate modified with zinc acetate produced in accordance with Example 1 and claimed herein.

B represents a 6 ml (3ml draw) syringe which contains lithium heparin produced by Viobin Corporation.

C represents a 3 ml syringe (3 ml draw) produced by Radiometer A/S and marketed under the tradename Smooth-E Arterial Syringe. It contains a lithium heparin anticoagulant and additional anions as described previously herein.

The above data shows that samples collected with Syringe A exhibited good correlation coefficients relat- It can be seen through the mean value data set forth in Table 2 that Syringe A and B exhibited satisfactory results relative to the control syringe on both full draw and short draw samples. In contrast, samples collected with Syringe C exhibited a significantly higher potassium ion concentration at reduced blood draw volumes.

EXAMPLE 4

The procedure of Example 2 was repeated except that the samples were tested for total calcium concentration rather than ionized calcium concentration. The results of Example 4 are presented in Table 3.

TABLE 3

COMPARISION OF TOTAL CALCIUM CONCENTRATION OBTAINED WITH VARIED DRAW VOLUMES

| Syringe | Draw Volume mL | X (±SD)$^a$ mg/dL | Comparison to Plain Syringe | | | |
|---|---|---|---|---|---|---|
| | | | Slope | Intercept | Correl Coef | p = |
| A | 3.0 | 9.4 (±0.2) | 0.80 | 1.9 | 0.83 | 0.15 |
| | 1.0 | 9.3 (±0.2) | 0.79 | 2.2 | 0.81 | <0.01 |
| | 0.75 | 9.3 (±0.3)$^b$ | 0.60 | 4.1 | 0.63 | 0.04 |

TABLE 3-continued

COMPARISION OF TOTAL CALCIUM CONCENTRATION
OBTAINED WITH VARIED DRAW VOLUMES

| Syringe | Draw Volume mL | X (±SD)[a] mg/dL | Comparison to Plain Syringe | | | |
|---|---|---|---|---|---|---|
| | | | Slope | Intercept | Correl Coef | p = |
| B | 3.0 | 9.4 (±0.2) | 0.96 | 0.4 | 0.90 | 0.04 |
| | 1.0 | 9.3 (±0.2) | 0.84 | 1.7 | 0.82 | <0.01 |
| | 0.75 | 9.3 (±0.3)[c] | 0.19 | 7.6 | 0.36 | 0.31 |
| C | 3.0 | 9.9 (±0.3) | 0.67 | 2.0 | 0.70 | <0.01 |
| | 1.0 | 11.0 (±0.3) | 0.53 | 3.6 | 0.56 | <0.01 |
| | 0.75[b] | 11.4 (±0.4) | 0.38 | 5.1 | 0.67 | <0.01 |
| Control | | 9.5 (±0.2) | | | | |

[a] n = 10 for all syringe types.
[b] n = 4
[c] n = 7

It can be seen through the data set forth in Table 3 that the mean values of Syringe A and B were within 0.2 mg/dL relative to the plain syringe, even at reduced draw volumes. In contrast, the use of Syringe C yielded results which were modestly higher at full draw volumes and significantly higher at partial draw volumes. This demonstrates the artificial increase in total calcium values associated with the use of syringes such as Syringe C in partial draw blood sampling.

EXAMPLE 5 claimed herein were prepared. Each batch differed only in the amount of zinc acetate utilized. The batches used 3.0, 3.2, 4.0 and 5.0 grams of zinc acetate per 15 grams of initial sodium heparin.

The resulting heparin compositions were then placed within 6 ml (3 ml full draw) syringes per the procedure set forth in Example 2. Whole blood samples were then drawn in the various quantities noted in Tables 4, 5 and 6. Said samples were then analyzed for both ionized calcium concentrations and pH. The results of said analyis are also set forth in Tables 4, 5 and 6.

TABLE 4

| HEP. SALT MODIFICATION | WHOLE BLOOD TOTAL VOLUME PER SYRINGE (ml) | TOTAL HEPARIN units/syringe | IONIZED CALCIUM mg/dl | | | | pH | | | |
|---|---|---|---|---|---|---|---|---|---|---|
| | | | DONOR A | | DONOR B | | DONOR A | | DONOR B | |
| 3.0 grms ZnAc | 3.0 | 36 | 5.08 | 5.04 | 5.04 | 5.08 | 7.39 | 7.39 | 7.37 | 7.37 |
| | 1.5 | 72 | 5.04 | 5.00 | 5.00 | 5.04 | 7.39 | 7.39 | 7.37 | 7.36 |
| | 0.75 | 144 | 4.92 | 4.96 | 4.88 | 4.92 | 7.39 | 7.38 | 7.36 | 7.36 |
| | 0.43 | 251 | 4.72 | 4.68 | 4.68 | — | 7.38 | 7.37 | 7.36 | — |
| | 0.30 | 360 | 4.56 | 4.60 | 4.48 | 4.40 | 7.36 | 7.37 | 7.38 | 7.38 |
| 3.2 gms ZnAc | 3.0 | 36 | 5.04 | 5.00 | 5.04 | 5.04 | 7.39 | 7.39 | 7.37 | 7.36 |
| | 1.5 | 72 | 5.08 | 5.04 | 5.04 | 5.04 | 7.39 | 7.39 | 7.37 | 7.36 |
| | 0.75 | 144 | 4.96 | 4.96 | 4.92 | 4.92 | 7.39 | 7.39 | 7.37 | 7.36 |
| | 0.43 | 251 | 4.80 | 4.80 | 4.72 | 4.76 | 7.37 | 7.37 | 7.36 | 7.35 |
| | 0.30 | 360 | 4.68 | 4.68 | 4.44 | 4.52 | 7.37 | 7.36 | 7.35 | 7.36 |
| CONTROL (A) | 1.0 | none | 5.12 | | | | 7.38 | | | |
| CONTROL (B) | 1.0 | none | 5.12 | | | | 7.38 | | | |

TABLE 5

| HEP. SALT MODIFICATION | WHOLE BLOOD TOTAL VOLUME PER SYRINGE (ml) | TOTAL HEPARIN units/syringe | IONIZED CALCIUM mg/dl | | | | pH | | | |
|---|---|---|---|---|---|---|---|---|---|---|
| | | | DONOR C | | DONOR D | | DONOR C | | DONOR D | |
| 4.0 grms ZnAc | 3.0 | 36 | 4.88 | 4.92 | 5.00 | 5.12 | 7.40 | 7.40 | 7.41 | 7.40 |
| | 1.5 | 72 | 4.92 | 4.96 | 5.08 | 5.16 | 7.40 | 7.39 | 7.40 | 7.40 |
| | 0.75 | 144 | — | 4.92 | 5.04 | 5.12 | — | 7.39 | 7.40 | 7.40 |
| | 0.43 | 251 | 4.56 | 4.64 | 4.88 | 4.96 | 7.38 | 7.37 | 7.40 | 7.39 |
| | 0.30 | 360 | 4.48 | 4.44 | 4.68 | 4.76 | 7.36 | 7.36 | 7.39 | 7.39 |
| CONTROL (C) | 1.0 | none | 5.04 | | — | | 7.39 | | — | |
| CONTROL (D) | 1.0 | none | | | 5.12 | | | | 7.40 | |

The procedure of Example 1 was followed such that four (4) separate batches of the heparin composition

TABLE 6

| HEP. SALT MODIFICATION | WHOLE BLOOD TOTAL VOLUME PER SYRINGE (ml) | TOTAL HEPARIN UNITS ML | IONIZED CALCIUM mg/dl$^2$ | | | | pH | | | |
|---|---|---|---|---|---|---|---|---|---|---|
| | | | DONOR A | | DONOR B | | DONOR A | | DONOR B | |
| 5.0 grms | 3.0 | 30 | 5.04 | 5.00 | 5.04 | 4.96 | 7.39 | 7.39 | 7.44 | 7.44 |
| | | 42 | 5.00 | 4.96 | 5.00 | 5.00 | 7.43 | 7.43 | 7.44 | 7.44 |
| | 1.5 | 60 | 5.04 | 5.00 | 5.04 | 4.96 | 7.41 | 7.41 | 7.44 | 7.44 |
| | | 84 | 5.00 | 5.08 | 5.00 | 5.00 | 7.43 | 7.43 | 7.44 | 7.44 |
| | 0.75 | 120 | 5.00 | 5.00 | 5.00 | 4.96 | 7.42 | 7.42 | 7.44 | 7.44 |
| | | 168 | 4.96 | 5.00 | 4.96 | 4.96 | 7.41 | 7.41 | 7.43 | 7.43 |
| | 0.43 | 209 | 4.88 | 4.88 | 4.83 | 4.84 | 7.42 | 7.42 | 7.44 | 7.43 |

TABLE 6-continued

| HEP. SALT MODIFICATION | WHOLE BLOOD TOTAL VOLUME PER SYRINGE (ml) | TOTAL HEPARIN UNITS ML | IONIZED CALCIUM mg/dl$^2$ DONOR A | | DONOR B | | pH DONOR A | | DONOR B | |
|---|---|---|---|---|---|---|---|---|---|---|
| | | 293 | 4.72 | 4.68 | 4.76 | 4.72 | 7.39 | 7.40 | 7.42 | 7.42 |
| | 0.30 | 300 | 4.76 | 4.76 | 4.68 | 4.68 | 7.41 | 7.40 | 7.42 | 7.43 |
| | | 420 | 4.48 | 4.48 | 4.36 | 4.44 | 7.37 | 7.38 | 7.40 | 7.40 |
| CONTROL (C) | 1.0 | none | 5.04 | 5.08 | 5.00 | 5.00 | 7.40 | 7.40 | 7.44 | 7.44 |
| CONTROL (D) | 1.0 | none | 5.00 | — | 4.96 | 4.96 | 7.43 | — | 7.44 | 7.44 |

The results set forth in Tables 4–6 demonstrate the effectiveness of the claimed anticoaguant in not unduly decreasing the ionized calcium concentrations in sampled whole blood. It can be seen that the best results were obtained through the use of the most preferred composition, i.e. that produced with the use of 5 grams of zinc acetate per 15 grams of initial heparin.

We claim:

1. An apparatus for use in the collection of blood comprising:
   (1) a receptacle means defining a blood receiving space therein for receiving a blood sample;
   (2) a blood inlet means for introducing a blood sample into the blood receiving space; and
   (3) an anticoagulant present within said blood receiving space, said anticoagulant having been produced by a process comprising:
   a) contacting an aqueous solution of sodium heparin with an acidic ion exchange resin for a period sufficient such that aqueous effluent produced possesses a pH of about 3 or less;
   b) reacting said effluent with a heavy metal-containing compound suitable to produce a heavy metal heparin salt; and
   c) reacting said heavy metal heparin salt with an aqueous solution of lithium salts in sufficient amounts such that the resulting solution exhibits a pH of about 6 to about 7.

2. The apparatus of claim 1 further comprising filtering the solution resulting from step (c).

3. The apparatus of claim 1 wherein the solution utilized in step (a) has a concentration of about 30,000 to about 50,000 u/cc.

4. The apparatus of claim 1 further comprising drying the solution resulting from step (c).

5. The apparatus of claim 4 wherein the solution resulting from step (c) is dried by lyophilization.

6. The apparatus of claim 1 wherein the acidic ion exchange resin comprises a resin with a sulfonic acid functionality.

7. The apparatus of claim 6 wherein the acidic ion exchange resin is selected from the group consisting of IR-120 and IR-120 in the hydrogen form.

8. The apparatus of claim 1 wherein the heavy metal-containing compound comprises a zinc, barium or copper salt and the lithium salt is lithium hydroxide.

9. The apparatus of claim 8 wherein the heavy metal-containing compound is selected from the group consisting of zinc acetate dihydrate, zinc chloride, zinc sulfate, barium acetate, barium chloride, barium sulfate, copper acetate, copper chloride, cooper sulfate and mixtures thereof.

10. The apparatus of claim 1 selected from the group consisting of a capillary tube, syringe and vacuum container.

11. The apparatus of claim 10 wherein the apparatus comprises a syringe.

12. The apparatus of claim 1 wherein the heavy metal-containing compound comprises zinc acetate dihydrate.

13. The apparatus of claim 12 wherein zinc acetate dihydrate is utilized in amounts ranging from about 2 to about 7 grams per each 15 grams of sodium heparin used in step (a).

14. The apparatus of claim 13 wherein about 5 grams of zinc acetate dihydrate is utilized per each 15 grams of sodium heparin used in step (a).

15. An apparatus for use in the collection of blood comprising:
   (1) a receptacle means defining a blood receiving space therein for receiving a blood sample;
   (2) a blood inlet means for introducing a blood sample into the blood receiving space; and
   (3) an anticoagulant present within said blood receiving space, said anticoagulant having been produced by a process comprising:
   a) passing an aqueous solution of sodium heparin through a bed of an acidic ion exchange resin to produce an aqueous effluent having a pH of about 3 or less;
   b) reacting said aqueous effluent with zinc acetate dihydrate in amounts ranging from about 2 to about 7 grams per each 15 grams of sodium heparin used in step (a);
   c) reacting the product of step (b) with an aqueous solution of lithium hydroxide sufficient to produce a solution having a pH of about 6 to about 6.5;
   d) optionally, filtering the solution of step (c);
   e) optionally, drying the solution of either step (c) or step (d).

16. The apparatus of claim 15 wherein the solution of step (a) has a concentration of about 30,000 to about 50,000 u/cc.

17. The apparatus of claim 15 wherein zinc acetate dihydrate is utilized in step (b) in an amount of about 5 grams per each 15 grams of sodium heparin acid in step (a).

18. The apparatus of claim 15 wherein the solution of step (c) is filtered with a filter media having a pore size of about 0.22 microns.

19. The apparatus of claim 15 wherein the solution of step (c) or (d) is dried through lyophilization.

* * * * *